(12) United States Patent
Uehara

(10) Patent No.: US 11,701,003 B2
(45) Date of Patent: Jul. 18, 2023

(54) IMAGING APPARATUS, METHOD OF CONTROLLING IMAGING APPARATUS, COMPUTER PROGRAM, AND COMPUTER READABLE STORAGE MEDIUM

(71) Applicant: TERUMO KABUSHIKI KAISHA, Tokyo (JP)

(72) Inventor: Ryo Uehara, Ann Arbor, MI (US)

(73) Assignee: TERUMO KABISHIKI KAISHA, Tokyo (JP)

( * ) Notice: Subject to any disclaimer, the term of this patent is extended or adjusted under 35 U.S.C. 154(b) by 671 days.

(21) Appl. No.: 16/140,774

(22) Filed: Sep. 25, 2018

(65) Prior Publication Data

US 2019/0021599 A1   Jan. 24, 2019

Related U.S. Application Data

(63) Continuation of application No. PCT/JP2017/010705, filed on Mar. 16, 2017.

(30) Foreign Application Priority Data

Mar. 25, 2016  (JP) ................. 2016-062392

(51) Int. Cl.
*A61B 5/00* (2006.01)
*A61B 8/12* (2006.01)
(Continued)

(52) U.S. Cl.
CPC .......... *A61B 5/0035* (2013.01); *A61B 5/0066* (2013.01); *A61B 5/0084* (2013.01); (Continued)

(58) Field of Classification Search
CPC .... H03M 1/001; A61B 5/0035; A61B 5/0066; A61B 5/0084; A61B 8/12; A61B 8/54
See application file for complete search history.

(56) References Cited

U.S. PATENT DOCUMENTS 10,166,003 B2 *  1/2019  Mai .................... G01S 7/52085
10,433,733 B2 * 10/2019  Wang ................ A61B 5/14546
(Continued)

FOREIGN PATENT DOCUMENTS

JP    2014-180575 A    9/2014
JP    6566825 B2 *   8/2019
(Continued)

OTHER PUBLICATIONS

English Equivalent of JP6566825B2 (Year: 2015).*
(Continued)

*Primary Examiner* — Keith M Raymond
*Assistant Examiner* — Patrick M Mehl
(74) *Attorney, Agent, or Firm* — Buchanan Ingersoll & Rooney PC

(57) ABSTRACT

A pulse signal corresponding to rotation of an imaging core is input, and a repetition frequency of the input pulse signal is converted in accordance with the number of radially-aligned lines of an ultrasound tomographic image. Based on the pulse signal of which the repetition frequency has been converted, a drive signal for an ultrasound transceiver is generated to obtain an ultrasound tomographic image with the number of lines. A valid pulse is determined in accordance with the number of lines from the pulse signal of which the repetition frequency has been converted. A signal having a pulse train selected, based on the valid pulse from a pulse signal representing a cycle of a light source of light for interfering with the light from an optical transceiver is generated as a pulse signal representing a timing of sampling of an optical coherence signal for generating an optical tomographic image.

18 Claims, 6 Drawing Sheets

(51) Int. Cl.
*A61B 8/00* (2006.01)
*A61B 8/08* (2006.01)
*A61B 8/13* (2006.01)
*H03M 1/00* (2006.01)

(52) U.S. Cl.
CPC ............... *A61B 8/12* (2013.01); *A61B 8/54* (2013.01); *A61B 8/13* (2013.01); *A61B 8/5261* (2013.01); *H03M 1/001* (2013.01)

(56) References Cited

U.S. PATENT DOCUMENTS

| | | | | |
|---|---|---|---|---|
| 2012/0310081 A1* | 12/2012 | Adler | ................ | A61B 8/12 |
| | | | | 600/427 |
| 2014/0142404 A1* | 5/2014 | Wang | ................ | A61B 8/4416 |
| | | | | 600/324 |
| 2014/0187963 A1* | 7/2014 | Corl | ................ | H02P 6/06 |
| | | | | 600/467 |
| 2015/0005627 A1* | 1/2015 | Itoh | ................ | A61B 5/0084 |
| | | | | 600/427 |
| 2015/0086098 A1* | 3/2015 | Nair | ................ | G01S 15/8979 |
| | | | | 382/131 |
| 2016/0022248 A1 | 1/2016 | Mori et al. | | |
| 2016/0095577 A1 | 4/2016 | Itoh et al. | | |
| 2016/0228097 A1* | 8/2016 | Jaffer | ................ | A61B 8/5269 |
| 2019/0129026 A1* | 5/2019 | Sumi | ................ | G01S 15/8997 |

FOREIGN PATENT DOCUMENTS

| | | |
|---|---|---|
| WO | 2013/145690 A1 | 10/2013 |
| WO | 2014/162367 A1 | 10/2014 |
| WO | 2014/162368 A1 | 10/2014 |

OTHER PUBLICATIONS

International Search Report (PCT/ISA/210) dated May 30, 2017, by the Japanese Patent Office as the International Searching Authority for International Application No. PCT/JP2017/010705.

Written Opinion (PCT/ISA/237) dated May 30, 2017, by the Japanese Patent Office as the International Searching Authority for International Application No. PCT/JP2017/010705.

* cited by examiner

IMAGING APPARATUS, METHOD OF CONTROLLING IMAGING APPARATUS, COMPUTER PROGRAM, AND COMPUTER READABLE STORAGE MEDIUM

CROSS-REFERENCES TO RELATED APPLICATIONS

This application is a continuation of International Application No. PCT/JP2017/010705 filed on Mar. 16, 2017, which claims priority to Japanese Application No. 2016-062392 filed on Mar. 25, 2016, the entire contents of both of which is incorporated herein by reference.

TECHNICAL FIELD

The present disclosure generally relates to an imaging technology for diagnosis.

BACKGROUND DISCUSSION

Imaging apparatuses for diagnosis has been used for a diagnosis of arteriosclerosis, a preoperative diagnosis for medical treatment performed in a blood vessel with an advanced catheter such as a balloon catheter or a stent, or checking for a postoperative result.

The imaging apparatus for diagnosis includes an intravascular ultrasound (IVUS) diagnostic apparatus, an optical coherence tomography (OCT) diagnostic apparatus, and the apparatuses have different characteristics from each other.

In addition, recently, an imaging apparatus for diagnosis configured by combining a function of IVUS and a function of OCT has been proposed. The imaging apparatus for diagnosis includes an imaging core that rotatably accommodates an ultrasound transceiver which is capable of transmitting and receiving an ultrasound wave and an optical transceiver which is capable of transmitting and receiving light, at a distal position in a catheter. The imaging apparatus for diagnosis having both of the functions is capable of generating, with one scan, both of a cross-sectional image (ultrasound tomographic image) acquired by making use of characteristics of the IVUS by which it is possible to perform measurement to a high depth region and a cross-sectional image (optical tomographic image) acquired by making use of characteristics of the OCT by which it is possible to perform measurement with high resolution.

The imaging apparatus for diagnosis configured by combining the function of the IVUS and the function of the OCT has two completely different signal sources of the IVUS and the OCT. A trigger of an IVUS signal is generated in response to an encoder signal from a scanner motor in a motor drive unit (MDU). However, the trigger of the IVUS signal is synchronized with the imaging core in the catheter. On the other hand, a signal source of an OFDI signal is OFDI (optical unit), a trigger of the OFDI is based on wavelength sweeping, and thus it is difficult to synchronize the trigger of the OFDI with the scanner motor in the MDU.

SUMMARY

A technology is disclosed for acquiring synchronized ultrasound tomographic and optical tomographic images.

An imaging apparatus is disclosed for diagnosis that generates an ultrasound tomographic image and an optical tomographic image of a diagnosis target site of a subject by using a catheter which rotatably accommodates an imaging core provided with an ultrasound transceiver that transmits and receives an ultrasound wave and an optical transceiver that transmits and receives light, the imaging apparatus for diagnosis including: a motor drive unit that is connected to the catheter and rotates the imaging core; conversion means to which a pulse signal corresponding to rotation of the imaging core is input and which converts a repetition frequency of the input pulse signal in accordance with the number of radially-aligned lines configuring the ultrasound tomographic image; means that generates a drive signal for the ultrasound transceiver so as to obtain an ultrasound tomographic image with the number of lines, based on a pulse signal of which the repetition frequency has been converted by the conversion means, and that transmits the generated drive signal to the ultrasound transceiver via the motor drive unit; and generating means that determines a valid pulse in accordance with the number of lines from the pulse signal of which the repetition frequency has been converted by the conversion means and that generates, as a pulse signal representing a timing of sampling of an optical coherence signal for generating the optical tomographic image, a signal having a pulse train selected, based on the valid pulse from a pulse signal representing a cycle of a light source of light for interfering with the light from the optical transceiver.

In accordance with an aspect, an imaging apparatus is disclosed for diagnosis configured to generate an ultrasound tomographic image and an optical tomographic image of a diagnosis target site of a subject using a catheter which rotatably accommodates an imaging core provided with an ultrasound transceiver configured to transmit and receive an ultrasound wave and an optical transceiver configured to transmit and receive light, the imaging apparatus for diagnosis comprising: a motor drive unit that is connected to the catheter and configured to rotate the imaging core; a converter configured to receive a pulse signal corresponding to rotation of the imaging core and to convert a repetition frequency of the pulse signal in accordance with a number of radially-aligned lines of the ultrasound tomographic image; a transmitting and receiving board configured to generate a drive signal for the ultrasound transceiver and to obtain an ultrasound tomographic image with the number of radially-aligned lines, based on a pulse signal of which the repetition frequency has been converted by the converter, and configured to transmit the generated drive signal to the ultrasound transceiver via the motor drive unit; and a logic device configured to determine a valid pulse in accordance with the number of radially-aligned lines from the pulse signal of which the repetition frequency has been converted by the converter and configured to generate, as a pulse signal representing a timing of sampling of an optical coherence signal for generating the optical tomographic image, a signal having a pulse train selected, based on the valid pulse from a pulse signal representing a cycle of a light source of light for interfering with the light from the optical transceiver.

In accordance with another aspect, an imaging apparatus is disclosed for diagnosis configured to generate an ultrasound tomographic image and an optical tomographic image of a diagnosis target site of a subject by using a catheter which rotatably accommodates an imaging core provided with an ultrasound transceiver configured to transmit and receive an ultrasound wave and an optical transceiver configured to transmit and receive light, the imaging apparatus for diagnosis comprising: a motor drive unit that is connected to the catheter and configured to rotate the imaging core; a converter configured to receive a pulse signal corresponding to rotation of the imaging core and to convert a repetition frequency of the input pulse signal in accordance with a number of radially-aligned lines of the ultrasound tomographic image; a transmitting and receiving board configured to generate a drive signal for the ultrasound transceiver to obtain an ultrasound tomographic image with the number of radially-aligned lines, based on a pulse signal of which the repetition frequency has been converted by the converter, and configured to transmit the generated drive signal to the ultrasound transceiver via the motor drive unit; and a logic device configured to determine a valid pulse in accordance with the number of radially-aligned lines from the pulse signal representing a cycle of a light source of light for interfering with the light from the optical transceiver and configured to generate, as a pulse signal representing a timing of sampling of a signal of a reflected wave of the ultrasound wave from the ultrasound transceiver, a signal having a pulse train selected, based on the valid pulse from a pulse signal of which the repetition frequency has been converted by the converter.

In accordance with an aspect, a method is disclosed of controlling an imaging apparatus for diagnosis configured to generate an ultrasound tomographic image and an optical tomographic image of a diagnosis target site of a subject using a catheter which rotatably accommodates an imaging core having an ultrasound transceiver configured to transmit and receive an ultrasound wave and an optical transceiver configured to transmit and receive light, the imaging apparatus for diagnosis including a motor drive unit configured to be connected to the catheter and rotate the imaging core, the method comprising: inputting a pulse signal corresponding to rotation of the imaging core and converting a repetition frequency of the input pulse signal in accordance with the number of radially-aligned lines of the ultrasound tomographic image; generating a drive signal for the ultrasound transceiver to obtain an ultrasound tomographic image with the number of radially-aligned lines, based on a pulse signal of which the repetition frequency has been converted, and transmitting the generated drive signal to the ultrasound transceiver via the motor drive unit; and determining a valid pulse in accordance with the number of radially-aligned lines from the pulse signal of which the repetition frequency has been converted and generating, as a pulse signal representing a timing of sampling of an optical coherence signal for generating the optical tomographic image, a signal having a pulse train selected, based on the valid pulse from a pulse signal representing a cycle of a light source of light for interfering with the light from the optical transceiver.

In accordance with a further aspect, a method is disclosed of controlling an imaging apparatus for diagnosis that generates an ultrasound tomographic image and an optical tomographic image of a diagnosis target site of a subject by using a catheter which rotatably accommodates an imaging core provided with an ultrasound transceiver that transmits and receives an ultrasound wave and an optical transceiver that transmits and receives light, the imaging apparatus for diagnosis including a motor drive unit that is connected to the catheter and rotates the imaging core, the method comprising: inputting a pulse signal corresponding to rotation of the imaging core and converting a repetition frequency of the input pulse signal in accordance with the number of radially-aligned lines of the ultrasound tomographic image; generating a drive signal for the ultrasound transceiver so as to obtain an ultrasound tomographic image with the number of radially-aligned lines, based on a pulse signal of which the repetition frequency has been converted, and transmitting the generated drive signal to the ultrasound transceiver via the motor drive unit; and determining a valid pulse in accordance with the number of radially-aligned lines from the pulse signal representing a cycle of a light source of light for interfering with the light from the optical transceiver and generating, as a pulse signal representing a timing of sampling of a signal of a reflected wave of the ultrasound wave from the ultrasound transceiver, a signal having a pulse train selected, based on the valid pulse from a pulse signal of which the repetition frequency has been converted.

According to a configuration of the present disclosure, a technology for acquiring two synchronized ultrasound tomographic image and optical tomographic image is disclosed.

BRIEF DESCRIPTION OF THE DRAWINGS

The accompanying figures are included in the specification, constitute a part of the specification, represents embodiments of the present disclosure, and are used for the description of principles of the present disclosure, together with the description of the embodiments.

DETAILED DESCRIPTION

Hereinafter, embodiments of the present disclosure will be described in detail with reference to the accompanying drawings. Note that the embodiments described below, which are preferred specific examples of the present invention and thus include various technically preferable limitations, are not intended to limit the scope of the present disclosure, unless otherwise specified in the following description.

First Embodiment

Hereinafter, the embodiment according to the present disclosure will be described with reference to the accompanying figures. Note that, an imaging apparatus for diagnosis in this specification is described as an apparatus having both of an IVUS function and an OCT function.

Figure 1:
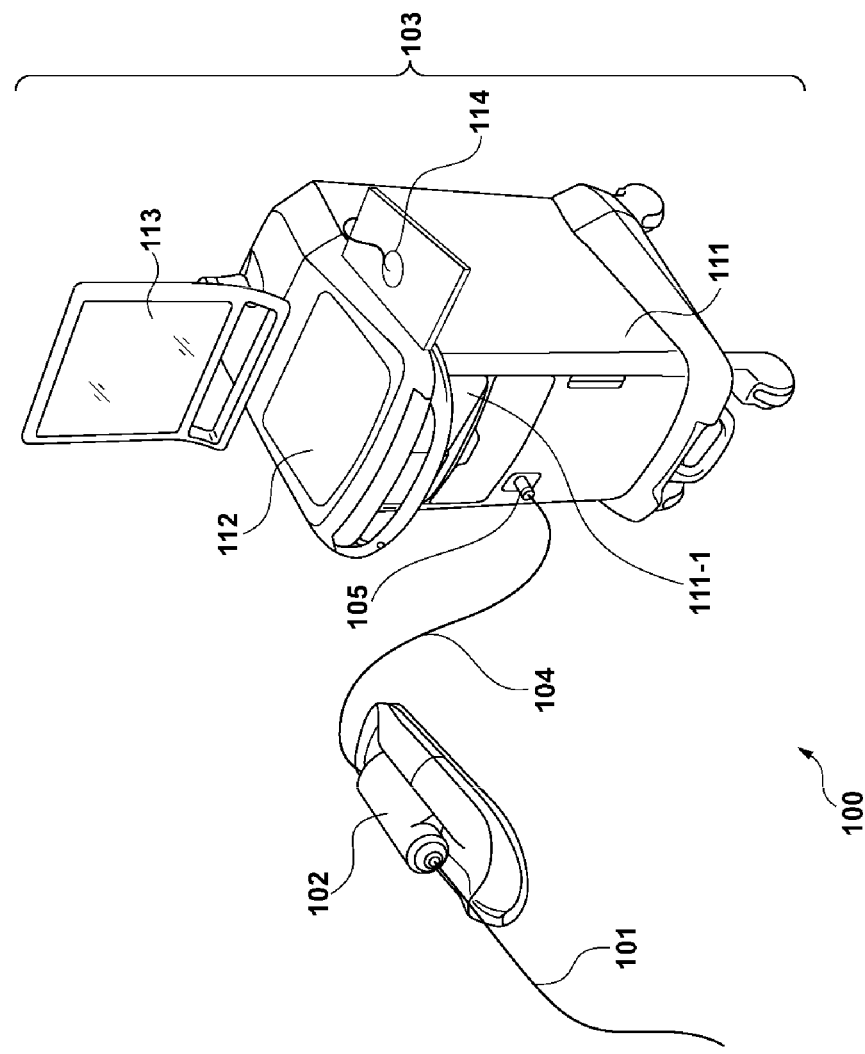
FIG. 1 is a view showing an example of the external appearance of an exemplary imaging apparatus for diagnosis.

FIG. 1 is a view illustrating an example of the external appearance of an exemplary imaging apparatus 100 for diagnosis according to the embodiment. As shown in FIG. 1, the imaging apparatus 100 for diagnosis includes a probe 101, a pull-back unit 102, and an operation control apparatus 103, and the pull-back unit 102 and the operation control apparatus 103 are connected to each other via a connector 105 through a cable 104 accommodating a signal wire or an optical fiber.

The probe 101 is directly inserted into a blood vessel, freely moves in a longitudinal direction of the blood vessel, and accommodates an imaging core that freely rotates. A distal end of the imaging core is provided with an ultrasound transceiver, which transmits an ultrasound wave based on a pulse signal and receives a reflected wave from the inside of the blood vessel, and an optical transceiver, which continuously transmits transferred light (measurement light) into the blood vessel and continuously receives the reflected light from the inside of the blood vessel. The imaging apparatus 100 for diagnosis measures a state of the inside of the blood vessel by using the imaging core.

The probe 101 is detachably attached to the pull-back unit 102, and the pull-back unit drives a built-in motor such that axial motion and rotational motion of the imaging core in a catheter inserted into the probe 101 in the blood vessel are defined. In addition, the pull-back unit 102 functions as a relay device of signals between the ultrasound transceiver and the optical transceiver in the imaging core and the operation control apparatus 103. In other words, the pull-back unit 102 has a function of transmitting an ultrasound drive signal from the operation control apparatus 103 to the ultrasound transceiver and transmitting, to the operation control apparatus 103, an electric signal representing a reflected wave from biological tissue detected by the ultrasound transceiver. In addition, the pull-back unit 102 has a function of transmitting the measurement light from the operation control apparatus 103 to the optical transceiver and transmitting, to the operation control apparatus 103, reflected light from biological tissue detected by the ultrasound transceiver.

The operation control apparatus 103 has a function for inputting various setting values and a function for processing ultrasound data or optical coherence data obtained by measurement and displaying various blood vessel images during the measurement.

In the operation control apparatus 103, 111 represents a main body control unit. The main body control unit 111 generates line data of lines parallel to a radial direction from a rotation center position based on a signal of a reflected wave of the ultrasound wave obtained by the measurement. In this manner, an ultrasound tomographic image is generated through interpolation processing of every line data. Further, the main body control unit 111 generates interference light data by causing reflected light from the imaging core to interfere with reference light obtained by splitting light from a light source and generates the line data by performing fast Fourier transform processing (FFT) on the interference light data. In this manner, an optical tomographic image can be generated through interpolation processing.

In accordance with an exemplary embodiment, 111-1 represents a printer and a DVD recorder. A process result in the main body control unit 111 is printed or the process result is written in a DVD, and thereby data (the ultrasound tomographic image, the optical tomographic image, imaging setting or imaging environment of each of the images, information for identifying an imaging target, or the like) is output to the outside. In addition, the printer and the DVD recorder also include an interface (not shown) such as a USB and outputs data from the USB to an external storage medium. In accordance with an exemplary embodiment, 112 represents an operation panel, and a user inputs various setting values and an instruction via the operation panel 112. In accordance with an exemplary embodiment, 113 represents an LCD monitor as a display apparatus, and various cross-sectional images generated in the main body control unit 111 are displayed thereon. In addition, 114 represents a mouse as a pointing device (coordinate input device).

Figure 2:
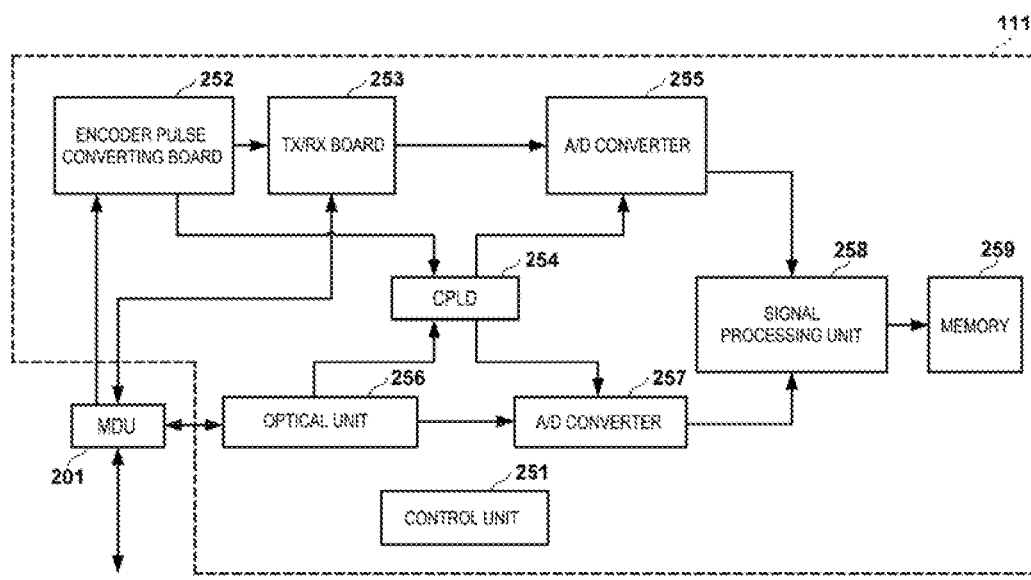
FIG. 2 is a block diagram showing an example of a configuration of a main body control unit.

Next, an example of a configuration of the main body control unit 111 will be described with reference to the block diagram as shown in FIG. 2. Note that FIG. 2 shows a main configuration for the following description. The main body control unit 111 may have a configuration that is not described nor shown in FIG. 2, and the description of a process by such a configuration is also omitted.

In accordance with an exemplary embodiment, a control unit 251 executes a process by using a computer program or data that is stored in a memory (not shown), thereby performing operation control of various functional units including units to be described below. In this manner, the control unit performs operation control of the entire main body control unit 111.

In accordance with an exemplary embodiment, a motor drive unit (MDU) 201 is connected to the catheter and rotates the probe 101. In an embodiment, the MDU operates at 1,800 rpm (revolutions per minute) and outputs a pulse signal of 1,024 pulse/rev (a pulse signal having 1,024 pulses per one rotation of the imaging core) as an encoder pulse signal.

An encoder pulse converting board 252 converts the encoder pulse signal from the MDU 201 into a pulse signal IVUS-TRG having a repetition frequency, which is set in advance and is selected from 512 pulse/rev (15.36 kHz), 1,024 pulse/rev (30.72 kHz), and 2,048 pulse/rev (61.44 kHz), and outputs the converted pulse signal IVUS-TRG to an IVUS (transmission and receiving board) (TX/RX) board 253 and a complex programmable logic device (CPLD) 254.

The TX/RX board 253 transmits, to an ultrasound transceiver via the MDU 201, a drive signal for generating an ultrasound wave by the ultrasound transceiver whenever a pulse from the encoder pulse converting board 252 is detected. On the other hand, the TX/RX board 253 transmits, to an ND (analog to digital) converter 255, a signal of a reflected wave of the ultrasound wave received from the ultrasound transceiver via the MDU 201. The TX/RX board 253 outputs signals of every line in an ultrasound image of 512 line/frame (one frame having 512 lines) in a case where 512 pulse/rev (15.36 kHz) is set as a conversion frequency in the encoder pulse converting board 252, the TX/RX board outputs signals of every line in an ultrasound image of 1,024 line/frame in a case where 1,024 pulse/rev (30.72 kHz) is set as the conversion frequency in the encoder pulse converting board 252, and the TX/RX board outputs signals of every line in an ultrasound image of 2,048 line/frame in a case where 2,048 pulse/rev (61.44 kHz) is set as the conversion frequency in the encoder pulse converting board 252. In addition, the encoder pulse converting board 252 acquires the number of radially-aligned lines of an ultrasound tomographic image that is generated from the ultrasound tomographic image.

An optical unit (OFDI) 256 outputs, to the CPLD 254, a pulse signal OFDI-TRG (pulse signal representing a cycle of a light source of wavelength sweeping light) having a frequency equal to that of a light source (light source generating light having a wavelength that changes at a predetermined cycle) of wavelength sweeping light that is supplied to the imaging core. Further, a reflected wave from the optical transceiver is guided to the optical unit 256 via the MDU 201, is mixed with light from the light source of wavelength sweeping light in the optical unit 256, and is light-received as interference light by a photodiode (not shown) in the optical unit 256. In this manner, the interference light light-received by the photodiode is photoelectrically converted, is amplified by an amplifier (not shown) in the optical unit 256, and then the photoelectrically converted and amplified interference light light-received by the photodiode is input to a demodulator (not shown) in the optical unit 256. The demodulator performs demodulation processing of picking out only a signal component of interfered light, and an output from the demodulation processing performed by the demodulator is input as an interference light signal to an A/D converter 257. In the embodiment, the optical unit 256 outputs a pulse signal of 82 kHz to the CPLD 254 and the optical unit 256 is set to generate an optical tomographic image of 512 line/frame.

The CPLD 254 outputs the pulse signal from the encoder pulse converting board 252 to the A/D converter 255 and outputs the pulse signal from the optical unit 256 to the A/D converter 257. Here, the CPLD 254 outputs the pulse signal from the encoder pulse converting board 252 to the A/D converter 255, as is; however, regarding the pulse signal from the optical unit 256, the CPLD does not output all of the pulses but a pulse input from the optical unit 256 immediately after a valid pulse is detected, to the A/D converter 257 when the valid pulse is detected from the pulses from the encoder pulse converting board 252.

The A/D converter 255 performs A/D conversion on "a signal of the reflected wave of the ultrasound wave corresponding to the pulse received from the CPLD 254", which the TX/RX board 253 has received from the ultrasound transceiver via the MDU 201 and transmits the A/D converted signal to a signal processing unit 258.

The A/D converter 257 does not perform A/D conversion unless receiving a pulse from the CPLD 254 and, when receiving the pulse from the CPLD 254, the A/D converter performs the A/D conversion on an interference light signal received from the optical unit 256, as an interference light signal corresponding the pulse, and transmits the A/D converted signal to the signal processing unit 258. In other words, the pulse signal that is supplied from the CPLD 254 to the A/D converter 257 is a pulse signal representing a timing of sampling of an optical coherence signal.

The signal processing unit 258 generates an ultrasound tomographic image based on the signal from the A/D converter 255 and generates an optical tomographic image based on the signal from the A/D converter 257. The signal processing unit 258 stores both of the generated tomographic images in a memory 259.

Next, an operation of the CPLD 254 will be described.

Case where 512 Pulse/Rev is Set as Conversion Frequency in Encoder Pulse Converting Board 252

In a case where 512 pulse/rev is set as the conversion frequency, the encoder pulse converting board 252 converts the encoder pulse signal of 1,024 pulse/rev from the MDU 201 into a pulse signal IVUS-TRG of 512 pulse/rev (repetition frequency of 15.36 kHz) and transmits the pulse signal IVUS-TRG to the TX/RX board 253 and the CPLD 254. Consequently, signals of reflected waves of ultrasound waves corresponding to the lines of an image of 512 line/frame are output from the TX/RX board 253. On the other hand, the CPLD 254 receives a pulse signal OFDI-TRG of 82 kHz from the optical unit 256.

Figure 3:
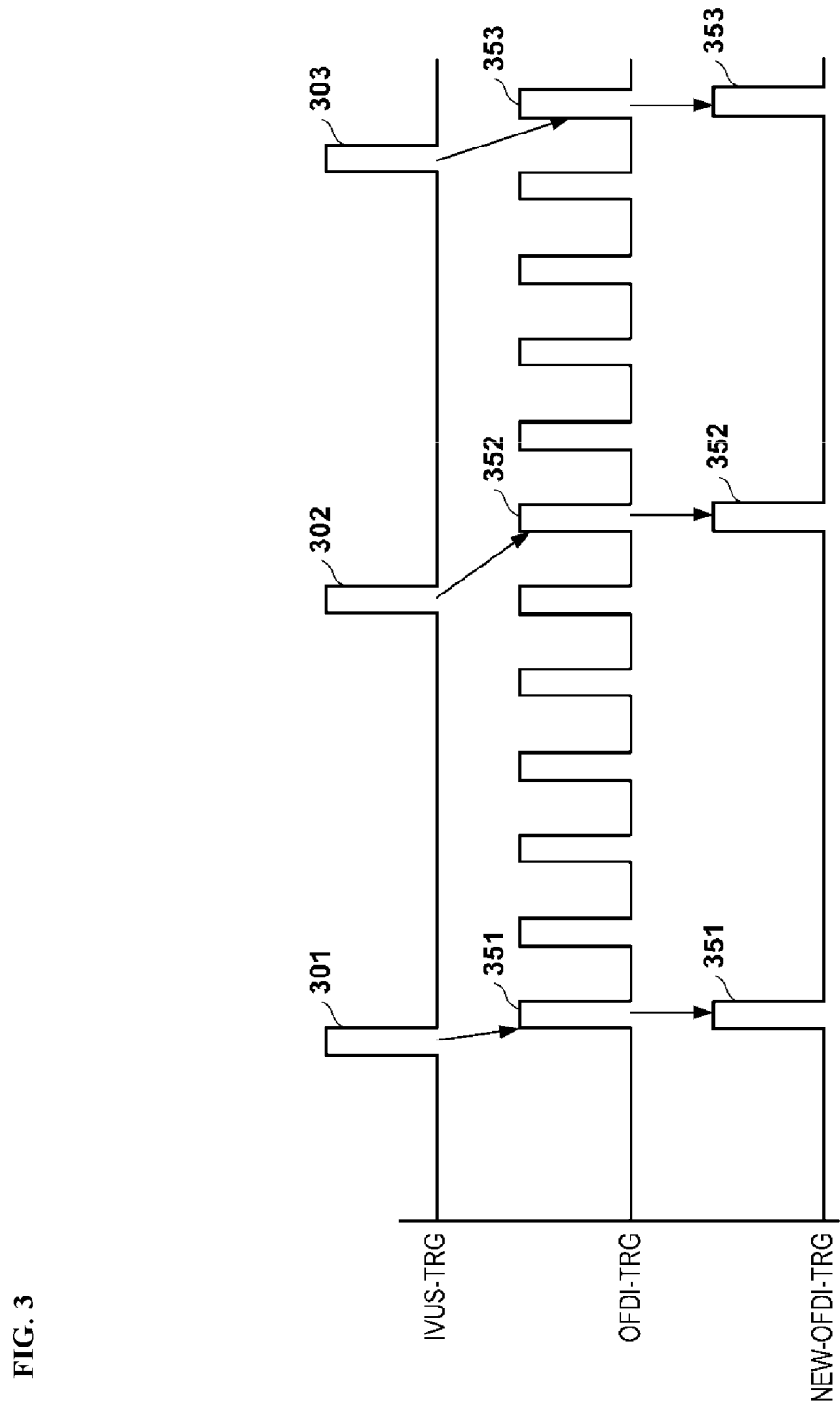
FIG. 3 is a diagram showing an example of pulse signals IVUS-TRG and OFDI-TRG.

FIG. 3 shows an example of pulse signals IVUS-TRG and OFDI-TRG which are input to the CPLD 254. In FIG. 3, a time axis is provided from left to right. In a case where the pulse signals IVUS-TRG and OFDI-TRG are input to the CPLD 254, the CPLD 254 outputs the pulse signal IVUS-TRG as is to the A/D converter 255. On the other hand, when a pulse of the pulse signal IVUS-TRG is detected, the CPLD 254 outputs, to the A/D converter 257, the pulse detected from the pulse signal OFDI-TRG immediately after the detection. In a case of FIG. 3, when a pulse 301 is detected in the pulse signal IVUS-TRG, a pulse 351 immediately after the pulse 301 is detected in the pulse signal OFDI-TRG is output to the A/D converter 257. In addition, when a pulse 302 is detected in the pulse signal IVUS-TRG, a pulse 352 immediately after the pulse 302 is detected in the pulse signal OFDI-TRG is output to the A/D converter 257. In addition, when a pulse 303 is detected in the pulse signal IVUS-TRG, a pulse 353 immediately after the pulse 303 is detected in the pulse signal OFDI-TRG is output to the A/D converter 257. A pulse signal representing a pulse train that the CPLD 254 outputs to the A/D converter 257 is represented by NEW-OFDI-TRG. As shown in FIG. 3, the pulse signal NEW-OFDI-TRG contains the pulses 351 to 353.

Case where 1,024 Pulse/Rev is Set as Conversion Frequency in Encoder Pulse Converting Board 252

In a case where 1,024 pulse/rev is set as the conversion frequency, the encoder pulse converting board 252 transmits the encoder pulse signal of 1,024 pulse/rev from the MDU 201, as is (without conversion), as the pulse signal IVUS-TRG (repetition frequency of 30.72 kHz), to the TX/RX board 253 and the CPLD 254. Consequently, signals of reflected waves of ultrasound waves corresponding to the lines of an image of 1,024 line/frame are output from the TX/RX board 253. On the other hand, the CPLD 254 receives the pulse signal OFDI-TRG of 82 kHz from the optical unit 256.

Figure 4:
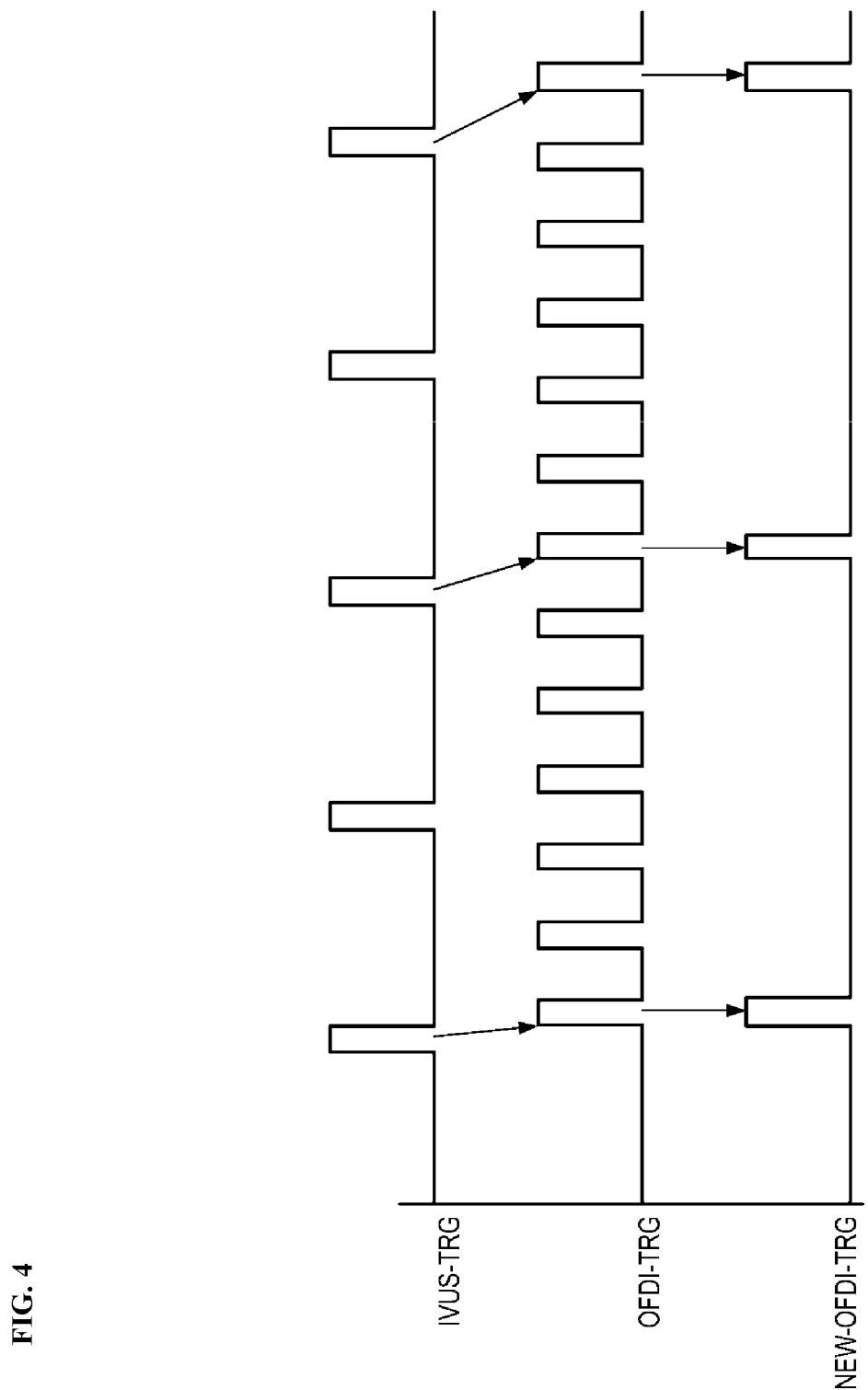
FIG. 4 is a diagram showing an example of pulse signals IVUS-TRG and OFDI-TRG.

FIG. 4 shows an example of pulse signals IVUS-TRG and OFDI-TRG which are input to the CPLD 254. In FIG. 4, a time axis is provided from left to right. In a case where the pulse signals IVUS-TRG and OFDI-TRG are input to the CPLD 254, the CPLD 254 outputs the pulse signal IVUS-TRG as is to the A/D converter 255. On the other hand, when a valid pulse is detected in the pulse signal IVUS-TRG, the CPLD 254 outputs, to the A/D converter 257, a pulse detected from the pulse signal OFDI-TRG immediately after the detection. More specifically, as shown in FIG. 4, when the CPLD 254 sets pulses of odd-numbered lines (or even-numbered lines) such as the first line (the first from left), the third line, the fifth line, and continuing similarly in the pulse signal IVUS-TRG as the valid pulse and detects the valid pulse, the CPLD outputs, to the A/D converter 257, a pulse immediately after the detection in the pulse signal OFDI-TRG. In this manner, when the CPLD 254 sets, as a valid pulse, a {1+(1,024 (number of set lines of ultrasound image of one frame)/512 (number of set lines of optical tomographic image of one frame)×n}-th pulse (n is an integer equal to or larger than 0) in the pulse signal IVUS-TRG in one image and detects the valid pulse, the CPLD outputs, to the A/D converter 257, a pulse immediately after the detection in the pulse signal OFDI-TRG.

Note that, in a case where 512 pulse/rev is set as the conversion frequency, a {1+(512 (number of set lines of ultrasound image of one frame)/512 (number of set lines of optical tomographic image of one frame)×n}-th pulse (n is an integer equal to or larger than 0) in the pulse signal IVUS-TRG in one image is set as the valid pulse, and this means that all of the pulses in the pulse signal IVUS-TRG in one image are the valid pulses. A pulse signal representing a pulse train that the CPLD 254 outputs to the A/D converter 257 is represented by NEW-OFDI-TRG.

Case where 2,048 Pulse/Rev is Set as Conversion Frequency in Encoder Pulse Converting Board 252

In a case where 2,048 pulse/rev is set as the conversion frequency, the encoder pulse converting board 252 converts the encoder pulse signal of 1,024 pulse/rev from the MDU 201 into a pulse signal IVUS-TRG of 2,048 pulse/rev (repetition frequency of 61.44 kHz) and transmits the pulse signal IVUS-TRG to the TX/RX board 253 and the CPLD 254. Consequently, signals of reflected waves of ultrasound waves corresponding to the lines of an image of 2,048 line/frame are output from the TX/RX board 253. On the other hand, the CPLD 254 receives the pulse signal OFDI-TRG of 82 kHz from the optical unit 256.

Figure 5:
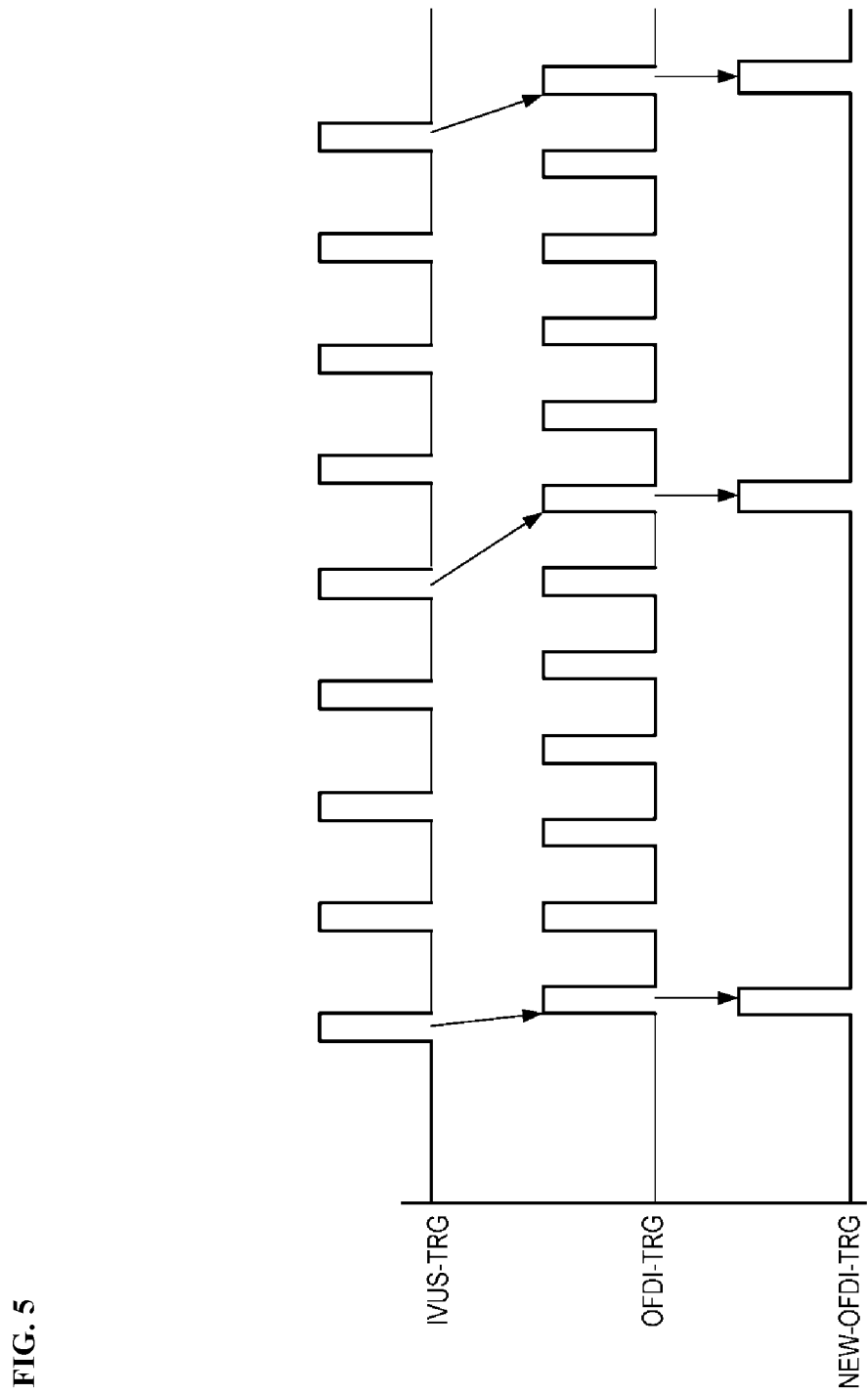
FIG. 5 is a diagram showing an example of pulse signals IVUS-TRG and OFDI-TRG.

FIG. 5 shows an example of pulse signals IVUS-TRG and OFDI-TRG which are input to the CPLD 254. In FIG. 5, a time axis is provided from left to right. In a case where the pulse signals IVUS-TRG and OFDI-TRG are input to the CPLD 254, the CPLD 254 outputs the pulse signal IVUS-TRG as is to the A/D converter 255. On the other hand, when a valid pulse is detected in the pulse signal IVUS-TRG, the CPLD 254 outputs, to the A/D converter 257, a pulse detected from the pulse signal OFDI-TRG immediately after the detection. More specifically, as shown in FIG. 5, when the CPLD 254 sets, as a valid pulse, a {1+(2,048 (number of set lines of ultrasound image of one frame)/512 (number of set lines of optical tomographic image of one frame)×n}-th pulse (n is an integer equal to or larger than 0) (or a {2+(2,048 (number of set lines of ultrasound image of one frame)/512 (number of set lines of optical tomographic image of one frame)×n}-th pulse) in the first line (first from left), the fifth line, the ninth line, and continuing similarly in the pulse signal IVUS-TRG in one image and detects the valid pulse, the CPLD outputs, to the A/D converter 257, a pulse immediately after the detection in the pulse signal OFDI-TRG. A pulse signal representing a pulse train that the CPLD 254 outputs to the A/D converter 257 is represented by NEW-OFDI-TRG.

Figure 6:
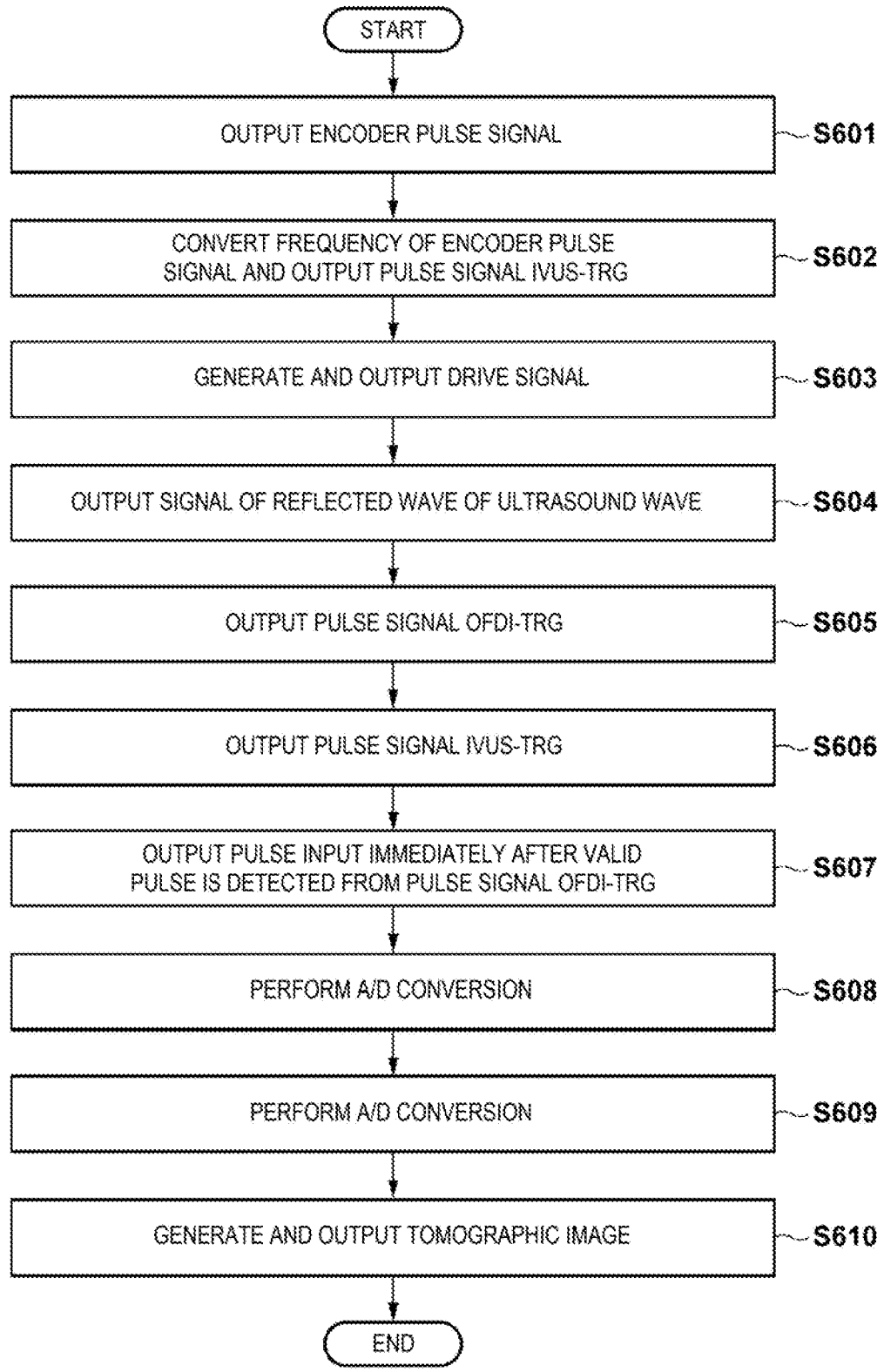
FIG. 6 is a flowchart of processes performed by the configuration of the block diagram in FIG. 2.

Processes performed by the configuration of the block diagram in FIG. 2 described above are described in accordance with a flowchart in FIG. 6.

In Step S601, the MDU 201 outputs the pulse signal of 1,024 pulse/rev as the encoder pulse signal to the encoder pulse converting board 252.

In Step S602, the encoder pulse converting board 252 converts the encoder pulse signal from the MDU 201 into a pulse signal IVUS-TRG having a preset repetition frequency and outputs the converted pulse signal IVUS-TRG to the TX/RX board 253 and the CPLD 254.

In Step S603, the TX/RX board 253 transmits, to the ultrasound transceiver via the MDU 201, the drive signal for generating the ultrasound wave by the ultrasound transceiver whenever the pulse from the encoder pulse converting board 252 is detected.

In Step S604, the TX/RX board 253 transmits, to the A/D converter 255, the signal of the reflected wave of the ultrasound wave received from the ultrasound transceiver via the MDU 201.

In Step S605, the optical unit 256 outputs, to the CPLD 254, the pulse signal OFDI-TRG having the frequency equal to that of the light source of wavelength sweeping light that is supplied to the imaging core.

In Step S606, the CPLD 254 outputs the pulse signal IVUS-TRG from the encoder pulse converting board 252 to the A/D converter 255.

In Step S607, when the CPLD 254 detects the valid pulse from the pulses from the encoder pulse converting board 252, a pulse input from the optical unit 256 immediately after the detection is output to the A/D converter 257.

In Step S608, the A/D converter 255 performs A/D conversion on "the signal of the reflected wave of the ultrasound wave corresponding to the pulse received from the CPLD 254", which the TX/RX board 253 has received from the ultrasound transceiver via the MDU 201 and transmits the A/D converted signal to the signal processing unit 258.

In Step S609, the A/D converter 257 performs A/D conversion on "the interference light signal corresponding to the pulse received from the CPLD 254" from the optical unit 256 and transmits the A/D converted signal to the signal processing unit 258.

In Step S610, the signal processing unit 258 generates line data of every line of the ultrasound tomographic image based on the signal from the A/D converter 255 and generates line data of every line of the optical tomographic image based on the signal from the A/D converter 257. The signal processing unit 258 stores, in the memory 259, the generated line data of every line of both of the ultrasound tomographic image and the optical tomographic image.

Note that, in FIG. 6, Steps S601 to S610 are performed in series; however, this does not mean only that the steps of Steps S601 to S610 are performed in this order in series. For example, the processes of Steps S601 to S604 and S606 and the process of Step S605 may be concurrently executed, or the process of Step S608 and the process of Step S609 may be concurrently executed.

Second Embodiment

In the first embodiment, when a valid pulse of the pulse signal IVUS-TRG is detected, the CPLD 254 outputs, to the A/D converter 257, a pulse detected from the pulse signal OFDI-TRG immediately after the detection. This means a configuration obtained by assuming that the pulse signal is output in real time to the A/D converter 255 and the A/D converter 257. If a restriction of the real time may be removed, the CPLD 254 may buffer the pulse signal OFDI-TRG in a memory not shown and may output, to the A/D converter 257, a pulse in the pulse signal OFDI-TRG at a timing approximate to a detection timing of the valid pulse in the pulse signal IVUS-TRG.

Third Embodiment

It is possible to switch between performing and nonperforming of a pulse output to the A/D converters 255 and 257 from the CPLD 254, that is, performing and nonperforming of an imaging start of the ultrasound tomographic image and the optical tomographic image in accordance with an instruction (user instruction) from a user. For example, in a case where the "instruction to start the ultrasound tomographic imaging and the optical tomographic imaging" is input as the user instruction by using a mouse 114 while the user refers to a setting screen displayed on a display apparatus 113, the CPLD 254 starts the pulse output to the A/D converters 255 and 257 in accordance with the user instruction. Here, in the embodiment, the CPLD 254 does not start the pulse output to the A/D converters 255 and 257 immediately when the user instruction is input and does not perform the pulse output to the A/D converters 255 and 257 until both of the pulse signals of the pulse signal IVUS-TRG from the encoder pulse converting board 252 and the pulse signal OFDI-TRG from the optical unit 256 come into a low state, but starts the pulse output to the A/D converters 255 and 257 when both of the pulse signals come into the low state. From here on, similarly to the above embodiment, the pulse output is continued until an "instruction to end the ultrasound tomographic imaging and the optical tomographic imaging" is received. Here, regarding a high state and a low state of the pulse signal, in a case of the pulse signal IVUS-TRG in FIG. 3, zones of the pulses 301, 302, and 303 can be defined as the "high state" and zones other than the pulses 301, 302, and 303 can be defined as the "low state", for example.

When the pulse output to the A/D converters 255 and 257 is started immediately when the user instruction is input, for example, the pulse signal IVUS-TRG is output as is to the A/D converter 255 in the subsequent stage even when the pulse signal IVUS-TRG during the input to the CPLD 254 is in the "high state" at the time when the user instruction is input. Therefore, an unintended output of the pulse signal to the A/D converter 255 and the A/D converter 257 in the subsequent stage is likely to occur. However, according to the configuration of the embodiment, it is possible to suppress the occurrence of the unintended pulse signal.

Fourth Embodiment

The conversion to a pulse signal of 512 pulse/rev (15.36 kHz), 1,024 pulse/rev (30.72 kHz), or 2,048 pulse/rev (61.44 kHz) in the encoder pulse converting board 252 may be set by, for example, using the mouse 114 while the user refers to the setting screen displayed on the display apparatus 113. In accordance with an exemplary embodiment, a method of setting the conversion repetition frequency is not limited to a specific setting method.

Fifth Embodiment

In the first to fourth embodiments, the valid pulse is determined in accordance with the conversion frequency from the pulse signal of which the repetition frequency has been converted by the encoder pulse converting board 252, and the signal having the pulse train selected, based on the valid pulse from the pulse signal representing the cycle of the light source of light for interfering with the light from the optical transceiver is generated as the pulse signal representing the timing of sampling of the optical coherence signal for generating the optical tomographic image. This is based on an assumption of a relationship of conversion frequency in encoder pulse converting board 252 less than (<) repetition frequency of light source of wavelength sweeping light that is supplied to imaging core. If there is a relationship of conversion frequency in encoder pulse converting board 252 greater than (>) repetition frequency of light source of wavelength sweeping light that is supplied to imaging core, a valid pulse may be determined in accordance with the conversion frequency from the pulse signal representing the cycle of the light source of the wavelength sweeping light that is supplied to the imaging core, and the signal having the pulse train selected, based on the valid pulse from the pulse signal, of which the repetition frequency has been converted by the encoder pulse converting board 252, may be generated as the pulse signal representing the timing of sampling of the signal of the reflected wave of the ultrasound wave from the ultrasound transceiver.

In addition, the numerical values used in the above description are examples used for the specific description, and the operations of the first and second embodiments are not limited to the numerical values.

In addition, the "signal sampling" used in the embodiments may be construed as sampling of a necessary signal from the input signals or may be construed as sampling of a necessary signal from stored signals when the input signals are stored as acquired signals.

In addition, regarding the "pulse signal corresponding to the rotation of the imaging core", in a case of the embodiments, the pulse signal is described to be emitted from the MDU 201; however, the pulse signal is not limited to being emitted from the MDU 201. For example, the catheter may actively emit the pulse signal.

In addition, in the embodiments, the {1+(number of set lines of ultrasound image of one frame/number of set lines of optical tomographic image of one frame)×n}-th pulse (n is an integer equal to or larger than 0) in the pulse signal, of which the repetition frequency has been converted, is set as the valid pulse. However, a case where the ratio between the number of set lines of the ultrasound image of one frame and the number of set lines of the optical tomographic image of one frame is not an integer is also considered. For example, in a case where the ratio is 3/2, two pulses of three continued pulses in the pulse signal, of which the repetition frequency has been converted, may be used as the valid pulse. In addition, when the valid pulse is selected by employing an integer part in the ratio, the number of times of selection of the valid pulse×"fraction part of ratio" exceeds 1, one adjacent pulse may be more selected as the valid pulse exceptionally (the number of times of selection of the valid pulse is initialized to 0 after the valid pulse is selected exceptionally). Otherwise, various methods of generating a new line by complementing the acquired lines are considered.

As described above, regarding the processes described above, the control unit 251 performs the operation control of the units by executing the processes by using the computer program or data. In this manner, since the units operate, and thereby the functions of the units are realized, a computer program is included in the scope of the present application of the disclosure. In addition, in general, since the computer program is stored in a computer readable storage medium such as a CD-ROM or a DVD-ROM, is set in a reading device (CD-ROM driver or the like) included in a computer, and can be executed by being copied or installed in a system, it is obvious that the computer-readable storage medium is also included in the scope of the present application of the disclosure.

The detailed description above describes an imaging technology for diagnosis. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus configured to generate an ultrasound tomographic image and an optical tomographic image of a target site of a subject using a catheter which rotatably accommodates an imaging core provided with an ultrasound transceiver configured to transmit and receive an ultrasound wave and an optical transceiver configured to transmit and receive light, the imaging apparatus comprising:
   a motor drive unit configured to be connected to the catheter and to rotate the imaging core;
   a converter configured to receive a pulse signal corresponding to rotation of the imaging core and to convert a repetition frequency of the pulse signal into a converted pulse signal in accordance with a set number of radially-aligned lines configuring one frame of the ultrasound tomographic image;
   a transmitting and receiving board configured to generate a drive signal for the ultrasound transceiver and to obtain the ultrasound tomographic image with the set number of radially-aligned lines based on the converted pulse signal to transmit the generated drive signal to the ultrasound transceiver via the motor drive unit; and a logic device configured to determine a valid pulse in accordance with the set number of radially-aligned lines from the converted pulse signal and to generate a pulse signal representing a timing of sampling of an optical coherence signal for generating the optical tomographic image having a pulse train selected, based on the valid pulse from a pulse signal representing a cycle of a light source generating light for interfering with light from the optical transceiver by setting from pulses in the converted pulse signal, as the valid pulse, a pulse according to a ratio between a number of set lines of the ultrasound image of one frame and a number of set lines of one frame of the optical tomographic image of one frame, selecting the pulse immediately after the valid pulse from the pulse signal representing the cycle of the light source, and generating a signal having the selected pulse train as the pulse signal representing the timing of the optical coherence signal.

2. The imaging apparatus according to claim 1, further comprising:
a first A/D (analog to digital) converter and a second A/D (analog to digital) converter, and wherein the transmitting and receiving board is configured to transmit to the first A/D converter a signal of a reflected wave of the ultrasound wave received from the ultrasound receiver via the motor drive unit.

3. The imaging apparatus according to claim 2, further comprising:
an optical unit configured to output to the logic device, a pulse signal having a frequency equal to that of the light source of wavelength sweeping light that is supplied to the imaging core.

4. The imaging apparatus according to claim 3, wherein the logic device is configured to output the pulse signal from the converter to the first A/D converter.

5. The imaging apparatus according to claim 4, wherein the logic device is configured to detect when the valid pulse from pulses from the converter, a pulse input from the optical unit immediately after the detection is output to the second A/D converter.

6. The imaging apparatus according to claim 5, wherein the first A/D converter is configured to perform an A/D conversion on the signal of the reflected wave of the ultrasound wave corresponding to the pulse received from the logic device, which the transmitting and receiving board has received from the ultrasound transceiver via the motor drive unit and transmits the A/D converted signal to a signal processing unit of a control unit.

7. The imaging apparatus according to claim 6, wherein the second A/D converter is configured to perform an A/D conversion on the pulse signal of the interference light corresponding to the pulse received from the logic device from the optical unit and to transmit the A/D converted signal to the signal processing unit of the control unit.

8. The imaging apparatus according to claim 7, wherein the signal processing unit is configured to generate line data of each line of the ultrasound tomographic image based on the signal from the first A/D converter and to generate line data of each line of the optical tomographic image based on the signal from the second A/D converter; and
wherein the signal processing unit of the control unit is configured to store the generated line data of each line of both of the ultrasound tomographic image and the optical tomographic image in a memory.

9. The imaging apparatus according to claim 1, wherein the pulse signal corresponding to the rotation of the imaging core is 512 pulse/rev (15.36 kHz), 1,024 pulse/rev (30.72 kHz), or 2,048 pulse/rev (61.44 kHz).

10. A non-transitory computer readable storage medium that stores the storing a computer program which, when executed by a computer processor causes the imaging apparatus according to claim 1 to generate the ultrasound tomographic image and the optical tomographic image of the target site of the subject using the catheter which rotatably accommodates the imaging core provided with the ultrasound transceiver to transmit and receive the ultrasound wave and the optical transceiver to transmit and receive light.

11. An imaging apparatus configured to generate an ultrasound tomographic image and an optical tomographic image of a target site of a subject using a catheter which rotatably accommodates an imaging core provided with an ultrasound transceiver configured to transmit and receive an ultrasound wave and an optical transceiver configured to transmit and receive light, the imaging apparatus comprising:
a motor drive unit configured to be connected to the catheter and to rotate the imaging core;
a converter configured to receive a pulse signal corresponding to rotation of the imaging core and to convert a repetition frequency of the pulse signal into a converted pulse signal in accordance with a set number of radially-aligned lines configuring one frame of the ultrasound tomographic image;
a transmitting and receiving board configured to generate a drive signal for the ultrasound transceiver and to obtain the ultrasound tomographic image with the set number of radially-aligned lines based on the converted pulse signal to transmit the generated drive signal to the ultrasound transceiver via the motor drive unit; and
a logic device configured to determine a valid pulse in accordance with the set number of radially-aligned lines from the converted pulse signal and to generate a pulse signal representing a timing of sampling of an optical coherence signal for generating the optical tomographic image having a pulse train selected, based on the valid pulse from a pulse signal representing a cycle of a light source generating light for interfering with light from the optical transceiver by setting from pulses in the converted pulse signal, as the valid pulse, a pulse according to a ratio between a number of set lines of the ultrasound image of one frame and a number of set lines of one frame of the optical tomographic image of one frame, and generating a signal having the selected pulse train as the pulse signal representing the timing of the optical coherence signal.

12. The imaging apparatus according to claim 11, further comprising:
a first A/D (analog to digital) converter and a second A/D (analog to digital) converter, and wherein the transmitting and receiving board is configured to transmit to the first A/D converter a signal of a reflected wave of the ultrasound wave received from the ultrasound receiver via the motor drive unit.

13. The imaging apparatus according to claim 12, further comprising:
an optical unit configured to output to the logic device, a pulse signal having a frequency equal to that of the light source of wavelength sweeping light that is supplied to the imaging core.

14. The imaging apparatus according to claim 13, wherein the logic device is configured to output the pulse signal from the converter to the first A/D converter.

15. The imaging apparatus according to claim 14, wherein the logic device is configured to detect when the valid pulse from pulses from the converter, a pulse input from the optical unit immediately after the detection is output to the second A/D converter.

16. The imaging apparatus according to claim 15, wherein the first A/D converter is configured to perform an A/D conversion on the signal of the reflected wave of the ultrasound wave corresponding to the pulse received from the logic device, which the transmitting and receiving board has received from the ultrasound transceiver via the motor drive unit and transmits the A/D converted signal to a signal processing unit of a control unit.

17. The imaging apparatus according to claim 16, wherein the second A/D converter is configured to perform an A/D conversion on the pulse signal of the interference light corresponding to the pulse received from the logic device from the optical unit and to transmit the A/D converted signal to the signal processing unit of the control unit.

18. The imaging apparatus according to claim 17, wherein the signal processing unit is configured to generate line data of each line of the ultrasound tomographic image based on the signal from the first A/D converter and to generate line data of each line of the optical tomographic image based on the signal from the second A/D converter; and
    wherein the signal processing unit of the control unit is configured to store the generated line data of each line of both of the ultrasound tomographic image and the optical tomographic image in a memory.

\* \* \* \* \*